| (12) | United States Patent<br>Nordstrom | (10) Patent No.: US 10,561,312 B2<br>(45) Date of Patent: **\*Feb. 18, 2020** |
|---|---|---|

| (54) | METHOD AND APPARATUS FOR ADMINISTERING A LOW LUMINANCE VISUAL DYSFUNCTION TEST |
|---|---|
| (71) | Applicant: Cheryl Nordstrom, Hinsdale, IL (US) |
| (72) | Inventor: Cheryl Nordstrom, Hinsdale, IL (US) |
| ( * ) | Notice: Subject to any disclaimer, the term of this patent is extended or adjusted under 35 U.S.C. 154(b) by 0 days.<br>This patent is subject to a terminal disclaimer. |
| (21) | Appl. No.: 15/832,754 |
| (22) | Filed: Dec. 5, 2017 |
| (65) | Prior Publication Data<br>US 2018/0160896 A1  Jun. 14, 2018 |

Related U.S. Application Data

(63) Continuation-in-part of application No. 14/702,361, filed on May 1, 2015, now Pat. No. 9,833,137.

(Continued)

(51) Int. Cl.
*A61B 3/00* (2006.01)
*A61B 3/02* (2006.01)
(Continued)

(52) U.S. Cl.
CPC ............ *A61B 3/022* (2013.01); *A61B 3/0008* (2013.01); *A61B 3/0033* (2013.01);
(Continued)

(58) Field of Classification Search
CPC ....... A61B 3/022; A61B 3/032; A61B 3/0008; A61B 3/0033; A61B 3/0041; A61B 3/005;
(Continued)

(56) References Cited

U.S. PATENT DOCUMENTS

| 4,155,632 A | * | 5/1979 | Wolbarsht | ............. | A61B 3/032<br>351/232 |
|---|---|---|---|---|---|
| 2004/0027538 A1 | * | 2/2004 | Sinclair | .................. | A61B 3/028<br>351/224 |

(Continued)

OTHER PUBLICATIONS

Wu, Zhichao, et al., Low Luminance Visual Acuity and Microperimetry in Age-Related Macular Degeneration, Article in Press Ophthalmology, 2014.

(Continued)

*Primary Examiner* — Jordan M Schwartz
(74) *Attorney, Agent, or Firm* — Simpson & Simpson, PLLC (57) ABSTRACT

A method for administering a low luminance dysfunction vision test by displaying, a first character at a first acuity level on a display at a first luminance level, receiving an input signal from the patient indicating whether the patient recognizes the first character, displaying a second character at a second acuity level and the first luminance level, receiving a second input signal from the patient indicating whether the patient recognizes the second character, calculating a first score, displaying a third character at a third acuity level and a second luminance level, which luminance level replicates a specific low luminance real environmental condition, receiving a third input signal from the patient indicating whether the patient recognizes the third character, displaying a fourth character at a fourth acuity level and the second luminance level, receiving a fourth input signal from the patient indicating whether the patient recognizes the fourth character, calculating a second score and calculating a third score.

16 Claims, 2 Drawing Sheets

Related U.S. Application Data (60) Provisional application No. 61/987,986, filed on May 2, 2014.

(51) Int. Cl.
*A61B 3/028* (2006.01)
*A61B 3/032* (2006.01)
*A61B 3/06* (2006.01)

(52) U.S. Cl.
CPC ............ *A61B 3/0041* (2013.01); *A61B 3/028* (2013.01); *A61B 3/032* (2013.01); *A61B 3/06* (2013.01)

(58) Field of Classification Search
CPC ......... A61B 3/0091; A61B 3/02; A61B 3/028; A61B 3/0325; A61B 3/06; A61B 3/063
See application file for complete search history.

(56) References Cited

U.S. PATENT DOCUMENTS

| | | | | |
|---|---|---|---|---|
| 2008/0204662 A1* | 8/2008 | Kanazawa | ............ | A61B 3/032 351/243 |
| 2013/0293846 A1 | 11/2013 | Nordstrom et al. | | |
| 2014/0218692 A1 | 8/2014 | Nordstrom et al. | | |
| 2014/0285769 A1* | 9/2014 | Palanker | ................ | G06Q 50/22 351/223 |

OTHER PUBLICATIONS

Sunness, Janet S., et al., Low Luminance Visual Dysfunction as a Predictor of Subsequent Visual Acuity Loss from Geographic Atrophy in Age-Related Macular Degeneration, Ophthalmology, vol. 115, No. 9, 2008, pp. 1480-1488.

Lad, Eleonora M, et al., Evaluation of Visual Function Impairments in Patients with Early and Intermediate Dry Age-Related Macular Degeneration, Duke University Medical Center, Durham, NC, United States, 2014.

Smith Kettlewell Institute, Low Luminance Visual Acuity (pp. 49-52), Feb. 14, 2013, Appendix C: Low Luminance Visual Acuity, Version 3.0.

Lad, Eleonora M., Evaluation of visual function impairments in patients with early and intermediate dry age-related macular degeneration, Duke University Medical Center, May 10, 2013, pp. 1-4.

Lad et al., Evaluation of Visual Function Impairments in Patients with Dry Age-Related Macular Degeneration, Investigative Ophthalmology & Visual Science Apr. 2014, vol. 55.

http://www.datacolor.com/photography-design/product-overview/spyder5-family; SPYDER5tm, last accessed: Mar. 21, 2018.

* cited by examiner

Fig. 2

METHOD AND APPARATUS FOR ADMINISTERING A LOW LUMINANCE VISUAL DYSFUNCTION TEST

CROSS-REFERENCE TO RELATED APPLICATIONS

This application is a continuation-in-part application filed under 35 U.S.C. §§ 111(a) and 120 of U.S. patent application Ser. No. 14/702,361, filed on May 1, 2015, which application is a non-provisional patent application claiming priority under 35 U.S.C. § 119(e) to U.S. Provisional Patent Application No. 61/987,986, filed May 2, 2014, which application is incorporated herein by reference in its entirety.

FIELD OF THE INVENTION

The invention broadly relates to eye tests for testing for low luminance visual dysfunction which may be used for the early detection, progress, treatment and monitoring of age-related macular degeneration (AMD) or other ocular diseases.

BACKGROUND OF THE INVENTION

Age-Related Macular Degeneration (AMD) is the leading cause of vision loss and blindness in the age group 65 and older. It is estimated that 6 million people in the United States alone are affected and with the aging Baby Boomer population, that figure is expected to grow at an explosive rate. AMD is a progressive disease with increased vision loss as the disease advances, particularly in the advanced stage. Drug companies are actively working to develop medications to slow or stop the advancement of dry AMD. In dry AMD, as opposed to wet AMD, cellular debris called drusen accumulates between the retina and the choroid, and the retina can become detached. There is a great need for a fast, repeatable, clinically-friendly test to serve as an end point in determining the efficacy of dry AMD treatment.

Most vision exams include a high-contrast visual acuity measurement. However, high-contrast visual acuity testing is ineffective in determining the presence or stage of dry AMD. Even advanced dry AMD patients may score at or near 20/20 visual acuity.

AMD patients often report difficulty seeing in dim lighting. "Even in the early stages of the disease when visual acuity is unaffected, these symptoms are present." Eleonora M. Lad, MD, PhD, *Evaluation of visual function impairments in patients with early and intermediate dry age related macular degeneration*. Research has shown that night vision loss may precede high-contrast visual acuity loss by two or more years in AMD patients and the difference in day and night vision may be able to not only identify AMD patients but identify the stage of disease as well as serve to be a predictive factor in identifying patients in the highest risk category for VA vision loss.

"The mechanism behind an increased LLD in eyes with AMD is not clearly understood. It has been suggested that [Low-Luminance Visual Acuity] LLVA most likely reflects central cone-mediated function under reduced illumination." Wu, Zhichao, et al., *Low-Luminance Visual Acuity and Microperimetry in Age-Related Macular Degeneration*, Article in Press Ophthalmology, 2014. For example, it is suggested that "[i]t is foveal (central) cone function in particular that is the most critical for preservation of (Visual Acuity). A reduction in foveal cone function in dim illumination reduces (Visual Acuity) dramatically." Janet S. Sunness, MD; Gary S. Rubin, PhD; Aimee Broman, MS; Carol A. Applegate, COT; Neil M. Bressler, MD; Barbara S. Hawkins, PhD, *Low Luminance Visual Dysfunction as a Predictor of Subsequent Visual Acuity Loss from Geographic Atrophy in Age-Related Macular Degeneration*, Ophthalmology, Volume 115, Number 9, September 2008.

It has also been suggested that night vision loss is "associated with decreased sensitivity of the rod system responsible for vision in the dark. This is consistent with pathology results in eyes with AMD that showed that the rod photoreceptors degenerate earlier than cones in most patients with early AMD, despite good visual acuity." Id.

A patient's visual function differential from day and night can be measured by comparing high-contrast visual acuity with low luminance visual acuity, or low-luminance deficit (LLD). There is a great need for an automatic, fast, friendly, repeatable Low Luminance Deficit test for use in both clinical trials as well as clinic.

Another study suggests that low luminance cone function may be another predictor of VA loss in AMD. This study reported, "cone dark-adapted function is affected more than cone function under photopic conditions." Id. "Studies often compare dark-adapted rod function to light-adapted cone function and don't capture cone function in dim illumination." Id.

This theory is furthered by another study which reports, "eyes with drusen with reduced dark-adapted foveal sensitivity to a small red stimulus, advanced AMD was more likely to develop." Id. Even though Dark Adaptation, or adapting the eyes to total darkness, has also been shown to be highly diagnostic for early AMD, it is a lengthy process, making it impractical to use in clinic. There is a need for a device to rapidly measure cone function in dim illumination without requiring dark adaptation. Research shows that patients with early AMD have a substantial recovery period for rods and cones to regain function in darkness after being exposed to light, known as "bleaching", as compared to normal patient population free of eye disease.

Dark Adaptation is a lengthy process, taking 10-20 minutes to complete. The length of time required makes its use in a busy clinic impractical at best.

Currently, two recognized methods exist for measuring Low Luminance Deficit—the early treatment diabetic retinopathy study (ETDRS) light box used with neutral density filters and the Smith Kettlewell Institute Low Luminance Acuity Card (or SKILL Card). Both methods are manual, time consuming, and prone to scoring errors.

ETDRS Light Box

The ETDRS light box consists of a retro-illuminated light box with florescent tubes and a sleeve covering each tube, serving as a baffle to reduce illumination. The tubes must be burned in for four days and replaced every year. New models use light-emitting diode (LED) lighting, eliminating the need for baffling. ETDRS chart letters are displayed on the outside of the box.

The procedure to calculate LLD consists of three parts administered under normal lighting conditions: 1. Measuring the best corrected high contrast VA by testing the patient with the ETDRS chart at 4 or 1 meters (to size the optotypes accordingly), 2. Measuring the best corrected low luminance visual acuity (LLVA) by testing the patient at 4 or 1 meters with the ETDRS light box at either 4 or 1 meters (to size the optotypes according to patient acuity) with neutral density filters covering patient or trial lenses; 3. Calculating the VA score, LLVA score and LLD using an ETDRS worksheet.

Several limitations exist with the ETDRS light box due to the variation in bulb illumination as well as the manual nature of the test. Limitations of the ETDRS light box include: variance in acuity levels due to memorization of letter sequence; variance in acuity level due to luminance level variation as a result of bulb life; potential operator bias due to prompting; scoring error due to manual calculations and manual comparison of VA scores; lack of test friendliness due to different test distances and manual score calculations; lack of interface to electronic medical records; manual comparison of patient test scores over time; no darkness progression testing due to a single low luminance comparison.

SKILL Card

The SKILL Card consists of an ETDRS letter card with letters on a white background on one side and letters on a dark gray background, designed to simulate a reduced luminance environment, on the other side.

The SKILL card procedure consists of three parts at near distance under normal light conditions: 1. Measuring and calculating the near VA by reading from side one of the card; 2. Measuring and calculating the near LLVA from reading from side two of the card; 3. Calculating the VA, LLVA and LLD using an ETDRS worksheet.

Several limitations exist with the SKILL card due to the manual presentation of the test as well as room luminance variability. Limitations of the SKILL card include: variance in acuity levels due to memorization of letter sequence; variance in acuity level due to luminance level variation at card, potential operator bias due to prompting; scoring error due to manual calculation and manual comparison of VA scores; lack of test friendliness due to manual calculations; lack of interface to electronic medical records; manual comparison of patient test scores over time; no darkness progression testing due to single low luminance comparison.

Auto-Refractor

The Auto-Refractor uses wavefront technology to perform a daytime and nighttime refraction. It is a structural test that measures the shape of the eye to provide an initial refraction to be checked by a physician. Low Luminance Deficit reports are not available.

There is a great need for a rapid, standardized, automatic Low Luminance Deficit test that can: Score LLVA; Serve as a Classification System for Dry AMD; Serve as an End-point for AMD Clinical Trials; and Determine the Efficacy of AMD Treatment.

BRIEF SUMMARY OF THE INVENTION

It is an object of the invention to provide a method for administering a low luminance dysfunction vision test to a patient using a computer, including the steps of displaying, in high contrast, a first character at a first acuity level against a display producing a first luminance level, which display is connected to the computer, receiving a first input signal from the patient via an input device, where the input signal is indicative of whether the patient recognizes the first character displayed in the first acuity level, displaying, in high contrast, a second character, being the same or different from the first character, the second character displayed at a second acuity level, differing from the first acuity level, against the display producing the first luminance level, receiving a second input signal from the patient via the input device, where the input signal is indicative of whether the patient recognizes the second character displayed at the second acuity level, calculating a first score based on the first and second input signals, the score corresponding to a first visual acuity of the patient in recognizing the first and second characters at the first and second acuity levels at the first luminance level, displaying a third character, being the same or different from the first and second characters, at a third acuity level against the display producing a second luminance level, the second luminance level being lower than the first luminance level and selected prior to administering the test to replicate a specific low luminance real environmental condition, where low acuity function in the specific low luminance real environmental condition is used as an indicator of a visual dysfunction, receiving a third input signal from the patient via the input device, where the third input signal is indicative of whether the patient recognizes the third character displayed at the third acuity level at the second luminance level, displaying a fourth character, being the same or different from the first, second, and third characters, at a fourth acuity level, against the display producing the second luminance level, receiving a fourth input signal from the patient via the input device, where the fourth input signal is indicative of whether the patient recognizes the fourth character displayed at the fourth acuity level at the second luminance level, calculating a second score based on the third and fourth input signals, the score corresponding to a second visual acuity of the patient for recognizing the third and fourth characters at the third and fourth acuity levels at the second luminance level, and calculating a degree of low luminance dysfunction by calculating a third score representing a difference between the first and second scores.

It is an additional object of the invention to provide a method for administering a low luminance dysfunction vision screening test to a patient using a computer, including the steps of displaying a first character at a first acuity level against a display connected to the computer and producing a low luminance level, which first acuity and low luminance levels are selected prior to administering the test to replicate a specific low luminance real environmental condition, such that failure to recognize the first character suggests a low luminance dysfunction in the patient, receiving a first input signal from the patient via an input device, where the first input signal is indicative of whether the patient recognizes the first character displayed at the first acuity level at the low luminance level, displaying a second character, being the same or different from the first character, at a second acuity level, against the display producing the low luminance level, receiving a second input signal from the patient via the input device, where the second input signal is indicative of whether the patient recognizes the second character displayed at the second acuity level at the low luminance level, and calculating a low luminance dysfunction screening score based on a comparison of first and second input signals with a set of predetermined normal vision values.

It is a further object of the invention to provide a method for displaying a simulated depiction of the vision of a patient with low luminance dysfunction, including the steps of receiving on a computer at least one low luminance dysfunction vision test record associated with the patient, displaying at least one sample image depicting normal vision in a specific visual environmental condition on a display attached to the computer, modifying the at least one sample image into at least one modified image according to a specific level of low luminance dysfunction recorded in the at least one low luminance dysfunction vision test record associated with the patient, such that the at least one modified image depicts the at least one sample image as it would been perceived by the patient in the specific visual environmental condition, and displaying the at least one modified image on the display.

The present invention is designed to calculate and track low luminance dysfunction under low light and night conditions. It calculates how much visual acuity loss a patient has in different environments. It may be a good indicator of dry AMD, making it a possible to show changes indicative to early, mid and late AMD, making it useful for both identifying the presence of dry AMD as well as determining the efficacy of treatment, including AMD drug treatment. U.S. patent application Ser. No. 14/251,286 (Nordstrom et al.) filed Apr. 11, 2014 is hereby incorporated by reference in its entirety.

The present invention includes: disease screening and management by physicians/technicians in the exam room in combination with other vision tests; disease screening and management by technicians in clinic screening rooms as a stand-alone test or combined with other vision tests; disease monitoring by patient at-home device with alerts or patient information sent to doctor.

The present invention includes a rapid functional self-test which quantifies Low Luminance Deficit and aids in predicting those patients most at risk for near-term visual acuity loss from AMD. For example, a particular increase in LLD can indicate early AMD or the advancement of AMD. Early AMD patients report having difficulty with night vision even with normal acuity function. Identifying patients with Low Luminance Deficit allows the clinician to proactively target patients that may benefit most from proactive treatment.

The method and apparatus for testing for low luminance deficit:

Provides rapid screening for Dry AMD;
Aids in identifying patients most at risk for AMD-related VA loss;
Compares patients results to AMD Stage Classification; and,
Helps determine efficacy of treatment.

The test for low luminance deficit measures both high-contrast and low luminance visual acuity using black and/or colored letters. Several luminance level options are available for testing in lighting similar to low restaurant lighting and night driving. The standard LLVA value presentation is consistent with the 100 fold reduction of the neutral density filters and SKILL card, providing Standardized Scores comparable to these methods. Unlike conventional methods, automatic scoring makes the test quick, easy and reliable.

Reports are presented in graphical format and are easy to interpret. Comparison Reporting of patient results over time allow for better management of disease progression and treatment efficacy.

The present invention is self-calibrating, providing standardized results that may be compared across devices and clinics. With further clinical trials, reports may be able to show results compared to AMD Stage Classification.

The present invention is available in three embodiments: Exam Lane, Screening Room, and At-Home.

The Exam Lane embodiment, or exam room embodiment, comprises a wall-mounted device coupled with a general purpose computer specially programmed for testing to be used in conjunction with acuity and other quality of vision tests, consolidating multiple testing capabilities into a single device. An "in-lane" embodiment is used in the ophthalmic lane along with other vision tests. This unit comprises a general purpose computer specially programmed for testing, a wireless input device, and a photometer, network interface software, and electronic medical records (EMR) interface software. Tests are taken at a distance and the computer is mounted on the wall in front of the patient. The user interface comprises a response monitor, tablet or keypad (preferably a wireless, touch-screen tablet or monitor) for the technician to input patient responses. Patient data can be stored encrypted on the local device for comparison reporting. If several ophthalmic lanes exist in a single practice, patient data can be stored on a network and accessed for comparing patient reports taken from several LLD devices. The system comprises a computer (including but not limited to desktop, laptop, notebook, tablet, or all-in-one versions), photometer (for example, the SPYDER5™ photometer available from DATACOLOR of Lawrenceville, N.J.), and custom software.

The Screening Room embodiment comprises a portable device coupled with a general purpose computer specially programmed for testing that isolates self-testing from the exam lane, thereby speeding up patient throughput. It communicates with EMR so results may be reviewed in the exam lane with the patient. A screening room device used in a screening room or waiting room comprises automated tests for the patient to administer with little or no supervision. This unit comprises custom testing software, a touch-screen tablet, optionally a separate photometer, network interface software and EMR interface software. The user interface comprises a response pad on the touch-screen device for patient use. Patient data can be stored encrypted on the local device for comparison reporting. If several screening room devices are in use within a practice, patient data can be sent to the server for comparison reporting.

The At-Home embodiment helps physicians better monitor a patient between visits. This embodiment comprises exception-oriented alerts to notify a doctor and patient that immediate care is needed. This may allow physicians to schedule AMD patients based on need as opposed to calendar, allowing them to focus on those patients that most need their care. Test results are stored in the cloud and may be pulled down by the clinic server to update EMR. An at-home device used by the patient at home to monitor his/her condition in between appointments. This unit comprises automated tests for the patient to administer with no supervision. This unit comprises customer testing software, a touch-screen tablet or phone, optionally a separate photometer, notification to the preferred clinic likely via Cloud Technology. The user interface comprises a response pad on the touch-screen device for patient use. Patient data is stored encrypted on the local device for comparison reporting. Exception-oriented alerts are sent to the clinic for immediate care. Activation of the device is controlled on a periodic basis to accommodate leasing. Activation of the device is controlled by an activation code obtained via website login. Activation may be by the number of uses or time period to accommodate leasing.

The Low Luminance Cone Function embodiment of the present invention presents dark colored letters as opposed to black letters on a dark gray background. The description above applies also to this embodiment.

Benefits over current technology include:
Rapid staircase testing;
Randomized presentation, eliminating cheating;
Letter, Number and Symbol presentation, allowing use in all populations;
Automated/Interactive presentation sequence, eliminating technician bias;
Interactive patient response, eliminating technician bias;

Automatic calculation of Visual Acuity Letter Score and Low Luminance Acuity Loss, eliminating human bias in scoring;

Fully calibrated, yielding consistent luminance and results over time;

Inexpensive/Cost effective;

Readily available; and,

May be bundled with other Quality of Vision and Acuity tests for more thorough evaluation.

BRIEF DESCRIPTION OF THE SEVERAL VIEWS OF THE DRAWING

The nature and mode of operation of the present invention will now be more fully described in the following detailed description of the invention taken with the accompanying drawing figures, in which.

DETAILED DESCRIPTION OF THE INVENTION

It is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Technical specifications are as follows:

The display is calibrated for contrast levels.

A test includes at least two passes:
  Pass A: high contrast visual acuity (VA); and
  Pass B: one or more low luminance visual acuity with different low luminance values.

The passes are scored.

The scores are compared to determine the loss of acuity at a specific low luminance level.

Letters, numbers or symbols are presented on a low luminance background.

Acuity levels can be presented in LogMAR acuity or Snellen acuity increments to standardize results to ETDRS Charts.

| LogMAR Acuity | Equivalence Chart |
|---|---|
| 20/800 | 1.6 |
| 20/640 | 1.5 |
| 20/500 | 1.4 |
| 20/400 | 1.3 |
| 20/320 | 1.2 |
| 20/250 | 1.1 |
| 20/200 | 1.0 |
| 20/160 | 0.9 |
| 20/125 | 0.8 |
| 20/100 | 0.7 |
| 20/80 | 0.6 |
| 20/63 | 0.5 |
| 20/50 | 0.4 |
| 20/40 | 0.3 |
| 20/32 | 0.2 |
| 20/25 | 0.1 |
| 20/20 | 0.0 |
| 20/16 | −0.1 |
| 20/12.5 | −0.2 |
| 20/10 | −0.3 |

The background luminance is presented at specific luminance in candela per meter squared, representing specific low light conditions, from dim indoor lighting (such as restaurant lighting) to moonlight. The first low luminance level for Pass B is 100 fold decrease in luminance over Pass A, simulating a neutral density filter worn over the patient's eye.

The specific luminance level may be selected by the administrator.

Test options include both near and distance.

Test options include monocular, single eye only, and binocular testing.

Letter size for acuity is sized for near testing at 18 inches, at distance testing based on lane length, or at standard 4 meters.

Each acuity level includes a plurality of letters, until the last acuity level presentation or a letter is missed, whichever comes first.

Target presentation times are of a fixed length, giving the patient a finite time to respond, ensure the test remains a rapid test.

Target presentation times may be set by the administrator based on the application-disease management versus super performance identification.

Beginning acuity level can be 1.0 LogMAR (or 20/200). In an example embodiment, the beginning acuity level can be 20/100.

Acuity levels decrease in 0.1 LogMAR steps (to ensure standardized results with existing clinical trials), with the test ending at 20/10 or a row in which four letters were identified incorrectly.

If twenty or fewer letters are identified correctly, the test continues upward in 0.1 LogMAR steps to 1.6 LogMAR or (20/800).

The staircase method reduces the acuity level by 0.2 LogMAR steps until a letter is missed.

Upon a miss, it increases the acuity level by 0.1 and continues to decrease in 0.1 Log units until the completion of the test.

Scoring is done for each eye, each pass is one point for each letter identified correctly, up to the acuity level 20/800 (even if the acuity levels higher than the ending acuity level were not presented). In the Staircase version, each acuity level presented represents five points if passed, even if only two letters were presented.

The acuity level for each eye, each pass is calculated on the point score.

Reporting calculates the Loss in Low Luminance Acuity by eye as the difference between Pass A and Pass B; Pass A and Pass C, etc.

Target Letter Presentation

In an example embodiment, the test for visual acuity presents randomized black ETDRS letters on a white background for VA testing and black ETDRS letters on a dark gray background. In an example embodiment, the Low Luminance Cone Function test presents randomized red, green or blue ETDRS letters on a dark gray background. The two tests function the same with the exception of the color of letters presented.

In an example embodiment, Snellen letters and/or non-character symbols may be used in the administration of the test. Examples of these non-character symbols include, but are not limited to, children's symbols, such as Allen Symbols, Lea Symbols or Patti Pics Symbols, as well as other ophthalmic symbols such as Tumbling Es or Landolt Cs. In the case of Tumbling Es or Landolt Cs, the responses would include left, right, up and down.

In an example embodiment, the patient may be required to dark adapt their eyes to low luminance ambient conditions prior to taking the low luminance portion of the test. For example, after completing the high contrast portion of the test, a message may appear on the display stating "The patient must be dark adapted before completing the remainder of the test. Please turn off the lights and have the patient remain in total darkness for 90 seconds." In another example embodiment, a countdown may appear on the display in dark red letters, so as not to interfere with dark adaptation, to serve as a timer for the dark adaptation process. In this example, the technician administering the test must press a start button on the screen or on a response pad to begin the countdown. In this example, a message appears on the screen or response pad stating "The patient must be dark adapted before completing the remainder of the test. Please turn off the lights and press the Start button. A counter will display the remaining time for dark adaptation." The system displays dark red numbers from 90 to 0 or 0 to 90, during which time the test will not proceed. After the dark adaptation has been completed, the test will continue with the low luminance portion of the test.

In an example embodiment, the background of the display is green, rather than dark gray. By changing the color to green, it is possible to replicate night vision goggle-aided vision. Accordingly, a night vision goggle test can be used to predict whether a person has normal or abnormal vision when wearing military night vision goggles. The night vision google test can optionally be calibrated for luminance and color prior to administration. The shade of green, as well as the luminance level, is specifically chosen to replicate vision using military night vision googles at dusk or dark.

Each night vision goggle letter is presented for a fixed number of seconds to both create a rapid test and ensure consistent test scores. The night vision goggle test uses a staircase presentation of visual acuity levels on one or more green low luminance backgrounds. The beginning visual acuity level may be lower than the starting LLD test as the test is designed for screening military personnel instead of patients with potential pathology. The staircase method decreases the acuity level by 2 levels until the patient misses a letter. Upon a miss, the VA level is increased by 1 level. The staircase protocol continues in the same fashion as the color vision test, varying the VA level in lieu of contrast level. The test ends at the lowest VA level the patient can see (3 out of 5 letters) for the green low luminance level. The test continues similarly for each green low luminance level. The test may or may not require the patient be dark adapted prior to beginning the night vision goggle test.

A response pad may be on-screen utilizing either red or black letters so as to not interfere with dark adaptation. Alternatively, responses may be entered via a wired or wireless response pad.

The night vision goggle report will list the lowest visual acuity level the patient can see for each eye for each green low luminance level. It may also show the range for normal night vision goggle performance or mild, moderate, or severe night vision goggle deficiency. It may also list the number of correct and incorrect responses per acuity level presented for each eye.

In an example embodiment, the LLD test is presented to the patient as an enclosed device. Specifically, the enclosed device includes the computer implementing the LLD test, the display to be viewed by the patient, a chin rest arranged at a predetermined distance from the display, and the input device. The patient places his forehead and chin on the chin rest and the characters or symbols are presented on the display. In an example embodiment, the enclosed device uses mirrors, projection or magnification to size the letters to the desired test distance. The enclosed device allows the distance LLD test to be administered in a much smaller area, such a pre-test or screening room and enforces a predetermined distance between the display and the patient's eyes.

Luminance Level

One or more luminance levels may be selected to represent different low luminance conditions, i.e., low restaurant lighting and night driving. The luminance level is selected at the beginning of the test and compared to high-contrast visual acuity. One luminance level can be set 100 times lower in luminance than the high contrast VA test so results may be compared to existing clinical trials using conventional methods described above.

Test Operation

The present invention comprises two passes: Pass A: high contrast visual acuity and Pass B: black letter low luminance visual acuity, with luminance level selected at the beginning of the test.

The low luminance cone function embodiment comprises two passes: Pass A: high contrast visual acuity and Pass B: colored letter low luminance visual acuity, with luminance level selected at the beginning of the test.

The background luminance is presented at specific luminance in candela per meter squared, representing specific low light conditions, from dim indoor lighting (such as restaurant lighting) to moonlight. In an example embodiment, the low luminance level of 0.5 $cd/m^2$ is selectable. Additionally, normal room lighting between approximately 100 and 150 $cd/m^2$ can be used.

The specific luminance level may be selected by the administrator at the beginning of the test.

In an example embodiment, the high contrast VA includes black lettering on a white background where the contrast >90% and the low luminance VA includes black lettering on a dark gray background constituting 1% of the reflectance of white.

Alternately, the LLD test may be performed as a low luminance visual acuity screening test. A separate low luminance screening mode allows for the quick determination of whether a patient has decreased low luminance vision and should be monitored with the full LLD test to determine the risk level of AMD Advancement. The low luminance screening mode presents only the LLVA portion of the LLD test, with a limited number (or a single line) of VA levels on one or multiple low luminance backgrounds. Letter presentation times are the same as the LLD test. Dark adaptation by the patient may be used in the low luminance screening mode.

The specific VA level presented is based on the low luminance visual acuity of patients with normal vision and without AMD or other pathology. If the patient is unable to see the letters at this VA level, the test results as considered abnormal. The low luminance screening report will display the lowest LLVA level the patient is able to see at the specific low luminance level for each eye and whether the results are "Normal" or "Abnormal Low Luminance Vision". If the patient has Abnormal Low Luminance Vision, the report will include a recommendation that the patient be monitored with the full LLD test. In an example embodiment, the low luminance screening test presents the entire LLVA portion of the LLD test, not limited to one or several visual acuity levels.

In an example embodiment, the Low Luminance Screening test requires dark adaptation to create a night vision test. A night vision test is useful to determine whether a non-AMD patient is having difficulty seeing in a low luminance setting. This test presents the LLVA portion of the LLD test to determine whether the patient may have abnormal low luminance vision and may have trouble seeing at dusk or at night, have difficulty with night driving, dusk or night walking, low luminance reading (such as in restaurant lighting), or other activities which may require safety decisions to be made by the physician. Safety decisions may include: DMV recommendations, increased night glasses prescriptions, reading lights, etc.

User Interface

Figure 1:
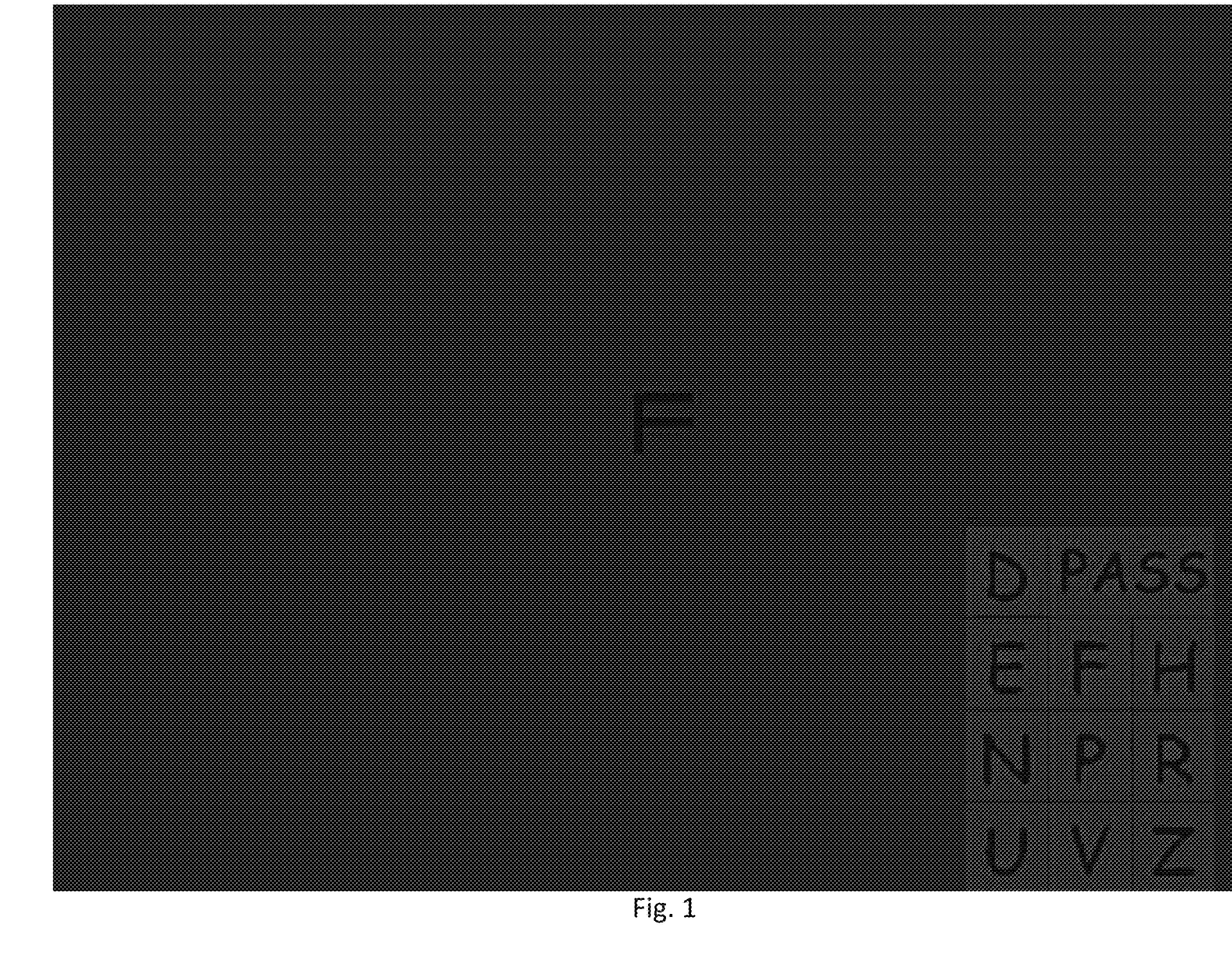
FIG. 1 is an example screen shot showing the invention with a response pad; and, FIG. 2 is an example screen shot showing the invention without a response pad.
Figure 2:
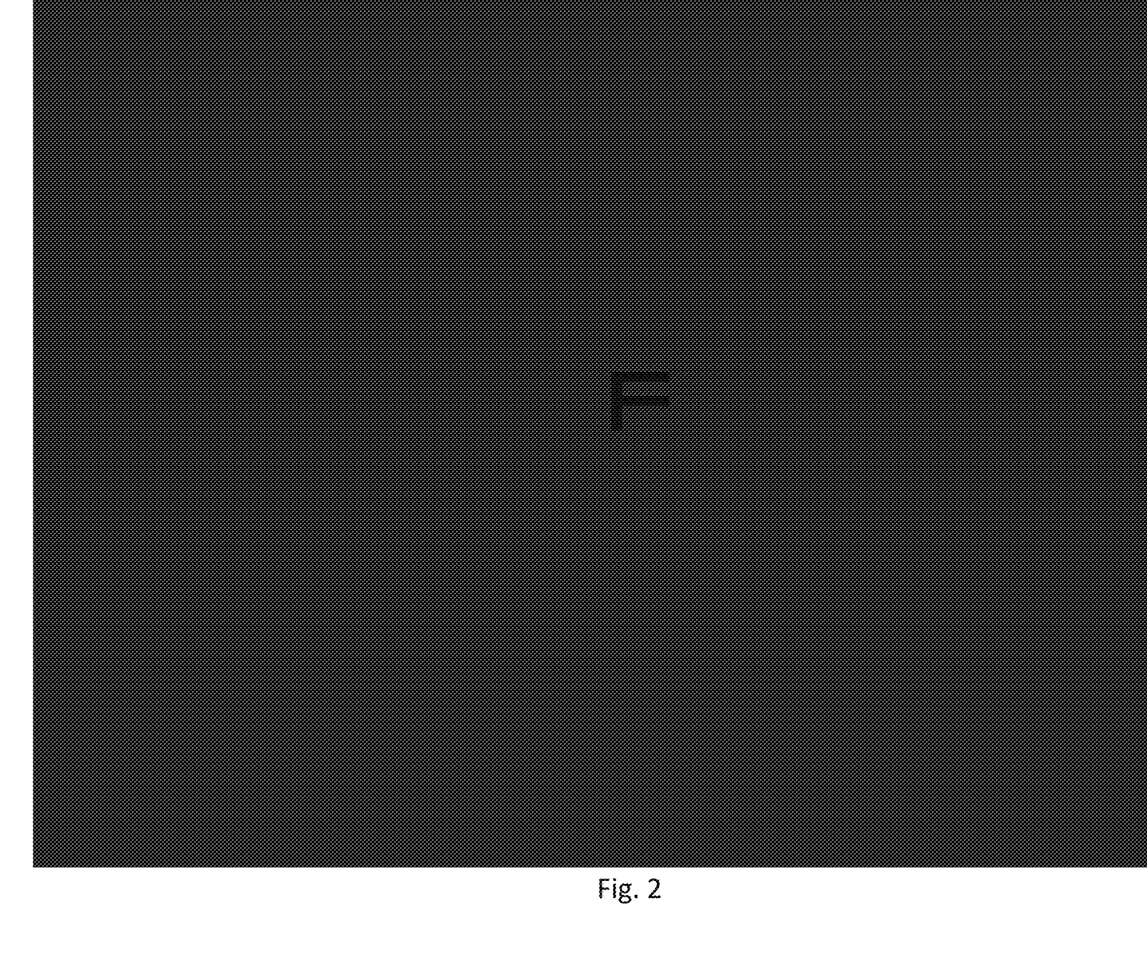

The patient responds via mouse click, touch screen or audibly to letters presented. The user interface comprises a response pad displayed on the display monitor, or a separate response device, such as a touchpad, an onscreen keyboard, wired or wireless keyboards, or wired or wireless keypads, or permitting a technician to input patient responses. It should be appreciated that in an example embodiment, the response pad is displayed alongside the letters presented as shown in FIG. 1. Alternatively, as shown in FIG. 2, the response pad can be displayed within a device separate and distinct from the letters presented.

In an example embodiment, the patient responds by verbally announcing the character or symbol displayed on the display monitor. In addition to the aforementioned case in which the technician enters the patient's verbal response, the patient's verbal response may be received by a microphone attached to the computer. Voice recognition software running on the computer then translates the patient's verbal response into a textual response identical to text input from a keyboard. Use of computer voice recognition is selectable and may be turned off on a case by case basis.

Additionally, it should be appreciated that the display pad can exhibit the possible responses against a backdrop having a greater contrast so that the patient can decipher the possible responses even if they cannot recognize the letter presented in low luminance. The response pad must be presented so the patient can see to respond without it interfering with the low-luminance test condition. The response pad may be a slightly lighter shade of gray or a colored background, such as red.

In an example embodiment, speakers, and wireless or wired headphones or headsets may be used to relay audible instructions or indications to the patient. Headphones may better accommodate both voice recognition and the voice confirmation of patient responses for patients at longer distances or in test environments in which multiple devices are being used in a small area.

Patient information, including identification, name and date of birth is collected for exam and comparison reporting. In addition to running the test and computing and storing the test results on a single computer, the test may be run on any of a number of networked or standalone computers, and the test results may be computed and/or stored on any of a network of computers. This arrangement ensures that a patient need not take a subsequent test on the same computer to ensure his record is present, and it allows for the sharing of the test results and patient records between computers in distant physical locations. The network of computers may include locally networked computers or computers connected through shared access to the Internet or a cloud of computers.

In an example embodiment, the computers implementing the LLD test use a sync function consisting of three steps: 1. identifying the LLD computers in the network to be synced into a central network database, 2. identifying and uploading the records from each LLD device on the network which need to be synced with the central network database; 3. identifying and download the records in the central network database which need to be downloaded and which local LLD device requires the download.

A sync file containing the practice name and unique device identifier for each LLD device is established as part of the setup of the central network database to control which devices get synced to the central network database. Proprietary sync software, located on the network, accesses all devices in the sync file network, syncs activity from the local databases into a single network database, and syncs each local device database with the contents of the central network database. The sync function can be scheduled for the same day and time or started manually. A sync timer setting is available as a system setting, residing on the network database which establishes the day and time for a scheduled sync.

An upload sync flag is part of the patient file as well as the patient test records file. Upon the completion of the addition or change to a patient record, the upload sync flag in the patient file is set to 1, flagging the file to be uploaded to the central network database upon the next sync. Upon the completion or deletion of a patient test, the patient test record upload sync flag is set to 1, flagging the file for upload to the central network database upon the next sync.

Upon the execution of the upload sync function, each uploaded patient or patient test record sync flag is set to 0, flagging the record as already synced. Download sync flag(s) 1 through x, based on the number of local LLD devices in the sync file, are also part of both the patient file as well as the patient test records file. As each record is uploaded to the network database, a download sync flag is set to the unique device identifier of the contributing LLD device.

Upon the download sync function, the first local LLD device in the sync file is accessed. Records in the central database that do not include the download sync flag for that local device are downloaded. After each record is downloaded to the local machine, the unique device identifier is added to the record on the central network database. Each local LLD device listed in the sync file is accessed in a similar manner. Since each record tracks the devices that have been synced, additional devices may be added at any point in time and are able to be synced into the network.

The patient test file also has a test device field. Upon the completion of the LLD test, the unique device identifier is recorded in the test device field. The test device field is used to identify the device on which the test was taken in the event that the test has erroneous or outlying results that may signify a device which needs to be recalibrated or otherwise serviced.

In an example embodiment, all records are copied to the central network database and repopulated to each local database. The integration of multiple devices within single location function is also used for automated VA, Cone Function, LLVA Screening, and Night Vision tests.

Calibration

The display is calibrated for color, luminance and contrast levels. Letters may be sized for near testing, for instance, at arms distance of 18 inches for touch screen monitors and for distance testing based on lane length.

Testing Options

Test options include both near distance and far distance. Test options include monocular, single eye only, and binocular testing. Test may be presented with letters, numbers or symbols. It should be appreciated that any character or symbol may suffice.

Staircase Methodology

Each acuity level presented comprises a total of five letters. Two letters are presented for each acuity level, until the last acuity level presentation or a letter is missed, whichever comes first. The last acuity level or any acuity level after an incorrect letter is identified comprises five letters. Beginning acuity level is 1.0 LogMAR (or 20/200), for example. If the patient responds correctly to two letters at a given acuity level, the acuity level decreases in 0.2 LogMAR units until a letter is missed or the last acuity level is presented. If the patient responds incorrectly to a letter at the initial acuity level, the acuity level increases in 0.1 LogMAR units until the patient correctly identifies all five letters on a given acuity level or the test reaches its highest acuity level of 1.6 LogMAR (or 20/800). If the patient responds incorrectly to a letter at an acuity level other than the initial acuity level, the acuity level increases by 0.1 LogMAR units and continues to decrease in 0.1 LogMAR units until the completion of the test.

Presentation Times

Target presentation times are of a fixed length, giving the patient a finite time to respond, ensuring the test remains a rapid test. Target presentation times may be set by the administrator based on the application, for example, disease management versus super performance identification.

Scoring

In an example embodiment, the total possible Raw Score for each eye is 100 points if patient correctly identifies all letters at the 20/10 level. Each acuity level passed without a miss is 5 points. Any partial acuity level is scored as one point for each letter correctly identified. Acuity levels which were skipped due to correctly identifying lower acuity levels receive 5 points per level. Low Luminance Deficit is the difference in raw score between the VA and LLVA. The raw score is presented along with the number of acuity levels differing between VA and LLVA with 5 points per level. Three points or more on a line rounds to the next acuity level.

Reporting

The Patient Exam Report shows for each eye: acuity lines presented, the number of letters presented and the number of correct responses for High Contrast VA and Low Luminance VA. For both VA and LLVA, the report may show the raw score, as well as the acuity level in LogMAR as described above. It also may show in graphical format the VA and the LLVA in LogMAR units as well as the LLD in LogMAR units. The Patient Comparison Report may show per eye: the VA, LLVA and LLD in LogMAR raw score over time. Significant VA, LLVA, or LLD degradation is alerted.

In an example embodiment, the test results, namely, the degree of low luminance dysfunction, are stored in an electronic health record (EHR) associated with the patient. An interface to EHR transfers patient test results from the LLD database to the EHR database. An interface from the computer systems implementing the LLD test to the computer systems storing EHR data ensures that all patient records are stored in a single location. Unlike the central network database and central cloud database which transfers LLD data to a central LLD database, the EHR interface transfers LLD data to an EHR database, allowing LLD data to be stored along with the patient's other medical records. The EHR interface is a one-way interface moving data only from the LLD database to the EHR database. An interface to EHR incorporates the transfer of individual test reports in a format such as .pdf, individual test scores, or both. For each test, the EHR interface transfers the patient's LLD test resulting including: patient name, test comments, LLD score left eye, VA left eye, LLVA left eye, LLD score right eye, VA right eye, and LLVA right eye.

The EHR interface is complementary to the integration of multiple LLD Devices over a computer network. Without the ability to store test data on the local LLD device or ensure it is accessible on the local LLD device, such as transferring it over the Internet or from a cloud of computers, progression analysis reports, a key component for patient management, would not be available.

In an example embodiment, at the conclusion of the patient test, the information is stored in a temporary EHR upload file. Upon the next sync function, all records in the temporary EHR upload file are transferred to the EHR. A DICOM interface is a standardized information format for patient records transfer. Transfer of data can be made directly to a specific EHR database or to EHR collection software, such as the MHS GENESIS® product used by the United States Department of Defense Military Health System.

In an example embodiment, a detailed exam report is generated after the completion of the LLD test. The LLD exam report graphically displays LLD scores per eye plotted against normal LLD, mild degradation, moderate degradation or severe degradation correlated with dry AMD advancement. Individual VA and LLVA scores are printed as supporting documentation for the LLD score for each eye to allow the physician to better evaluate the underlying factors of the LLD score.

A LLD progression report graphically displays the VA level, LLVA level(s) and LLD score(s) per eye over time. An alternate LLD Progression Report graphically displays only the LLD score(s) per eye over time.

An example of a report is shown below:

Innova Systems, Inc.
   Night Vision Report
      Patient Number:
      Patient Name:
      Date:

|  |  | Right Eye | | | | Left Eye | | | |
| --- | --- | --- | --- | --- | --- | --- | --- | --- | --- |
|  |  | VA | | LLVA | | VA | | LLVA | |
| Acuity | LogMAR | C | P | C | P | C | P | C | P |
| 20/100 | 0.7 | 2 | 2 | 2 | 2 | 2 | 2 | 2 | 2 |
| 20/80 | 0.6 |  |  |  | 2 | 2 |  |  |  |
| 20/63 | 0.5 | 2 | 2 | 2 | 5 | 1 | 2 | 2 | 2 |
| 20/40 | 0.3 | 2 | 2 | 2 |  |  | 2 | 2 | 2 |
| 20/32 | 0.2 | 5 |  |  |  |  |  |  | 5 |
| 20/25 | 0.1 | 0 | 2 | 2 |  |  | 2 | 2 | 2 |
| 20/20 | 0.0 |  | 5 | 4 |  |  | 5 | 4 |  |
| 20/10 | −.01 |  | 2 | 0 |  |  | 2 | 0 |  |
| Acuity Score |  | 84 | | 56 | | 84 | | 75 | |

Right Eye Low Luminance Deficit: 28/6 Acuity Lines
Left Eye Low Luminance Deficit: 9/2 Acuity Lines
Test Options:

Luminance Level: Night Driving- 1 cd/meter2
Test Distance: Near- 18 inches

In an example embodiment, the administration of the test is sped up by using a "learning" test algorithm based on the patient's last VA or LLD test results. The LLD test updates the patient's record automatically on completion of the LLD test. Alternately, the VA level may be entered manually from the patient's prior visual acuity exam. This learning test algorithm significantly reduces the number of visual acuity levels presented.

The following fields are included on the Patient Record to be accessed by the LLD test: Last VA left eye, Last VA right eye, Last LLVA (level 1) left eye, Last LLVA (level 1) right eye, Last LLVA (level 2), Last LLVA (level 2).

At the commencement of the LLD test, the patient record is read for VA and LLVA levels. If neither of these values are found, the LLD test uses a binary search sequence to determine the lowest VA the patient can see. The binary test algorithm is a rapid method to reach the patient's lowest visible VA over a wide range of acuity levels. The VA and LLVA presentations range from 20/10 to 20/1600, depending on the patient responses. The initial binary search may include a more limited range of visual acuity for the specific luminance level and are included only if the patient is unable to see lower acuity levels. Both the initial VA and initial LLVA acuity levels are standardized, but may differ from each other.

If any of the fields from the Patient Record listed above have a value, the starting points for the corresponding part of the test are altered. If a Last VA level is found on the patient record, the LLD test begins with a progressive value, e.g., 1-2 levels above the corresponding VA level for that eye. If a Last LLVA (level 1) is found, the LLD test begins the LLVA (levels 1) test with a VA level 1-2 levels about the Last LLVA (level 1) level for that eye. If a Last LLVA (level 2) value is found, the LLD test begins the LLVA (levels 2) test with a VA level 1-2 levels above the Last LLVA (level 2) level for that eye. If multiple values are found, the LLD test alters each corresponding part of the test.

If any of the fields from the patient record listed above have a value, the algorithm for the corresponding part of the test is also altered. Upon finding a value, the LLD test uses either a staircase algorithm to present VA or LLVA levels to reach the lowest acuity level which can be seen for the corresponding part of the test. The staircase algorithm increases or decreases the VA or LLVA level by 2 levels until the patient cannot see a specific level, then proceeds to a step algorithm until the patient reaches the lowest VA or LLVA level he can see. The algorithm for the VA, LLD (level 1), and LLD (level 2) can be altered individually or in combination based on the fields populated in the patient record.

In an example embodiment, a step algorithm may be used. The step algorithm increases or decreases the VA level one level at a time, based on patient input, until the patient reaches the lowest VA or LLVA level he can see.

Upon completion of the LLD test, the lowest visible VA and LLVA (level 1) and LLVA (level 2) for each eye are recorded in the Last VA and Last LLVA (level 1) and Last LLVA (level 2) on the Patient Record.

The Learning Algorithm may also apply to LLD, LLVA Screening, Night Vision Testing, Night Vision Goggle Testing, Automated VA Testing and Color Vision Testing.

Simulated Low Luminance Dysfunction

In an example embodiment, a patient's results in the low luminance dysfunction vision test can be used to create and display a simulated depiction of the patient's vision, so that people with normal vision can perceive how the low luminance dysfunction affects the patient's vision. Patients with decreased visual function often have difficulty communicating the vision loss they experience and how it impacts their daily living. This is especially true when their loss of vision has not yet impacted their visual acuity, i.e., they are 20/20 or near 20/20, but it is affecting their "quality of vision" (e.g., color vision, contrast sensitivity, low luminance vision). Family and caregivers may find it difficult to understand the patient's reduced abilities and may accordingly be unable to accommodate the patient for their abnormal vision. It is important for family or caregivers to better understand how the patient sees in specific situations so they can better aid the patient in these situations.

This simulated low luminance dysfunction is designed specifically for family members or caregivers to "experience" how the patient sees. It consists of a series of images which show the difference between how a normal person sees a particular image and how the patient sees that image. Images depicting normal color vision, normal low luminance vision, normal contrast vision, etc. are first displayed. Each of these images is then altered based on the specific patient's test scores for the color vision test, low luminance test, contrast sensitivity test, contract acuity test, etc. to demonstrate how the specific patient sees the same image(s). A single image may also be altered to combine the impact of the patient's test results from multiple tests into a single image.

It should be appreciated that the present invention can be combined with a cone contrast test in a single device for the early detection, progress, treatment and monitoring of age-related macular degeneration (AMD) or other ocular diseases.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A method for administering a low luminance dysfunction vision test to a patient using a computer, comprising the steps of:
   (a) displaying, in high contrast, a first character at a first acuity level against a display producing a first luminance level, which display is connected to the computer;
   (b) receiving a first input signal from the patient via an input device, where the input signal is indicative of whether the patient recognizes the first character displayed in the first acuity level;
   (c) displaying, in high contrast, a second character, being the same or different from the first character, the second character displayed at a second acuity level, differing from the first acuity level, against the display producing the first luminance level;
   (d) receiving a second input signal from the patient via the input device, where the input signal is indicative of whether the patient recognizes the second character displayed at the second acuity level;
   (e) calculating a first score based on the first and second input signals, the score corresponding to a first visual acuity of the patient in recognizing the first and second characters at the first and second acuity levels at the first luminance level;
   (f) displaying a third character, being the same or different from the first and second characters, at a third acuity level, being the same or different from the first and second acuity levels, against the display producing a second luminance level, the second luminance level being lower than the first luminance level and selected prior to administering the test to replicate a specific low luminance real environmental condition, where low acuity function in the specific low luminance real environmental condition is used as an indicator of a visual dysfunction;
   (g) receiving a third input signal from the patient via the input device, where the third input signal is indicative of whether the patient recognizes the third character displayed at the third acuity level at the second luminance level;
   (h) displaying a fourth character, being the same or different from the first, second, and third characters, at a fourth acuity level, being the same or different from the first, second, and third acuity levels, against the display producing the second luminance level;
   (i) receiving a fourth input signal from the patient via the input device, where the fourth input signal is indicative of whether the patient recognizes the fourth character displayed at the fourth acuity level at the second luminance level;
   (j) calculating a second score based on the third and fourth input signals, the score corresponding to a second visual acuity of the patient for recognizing the third and fourth characters at the third and fourth acuity levels at the second luminance level; and,
   (k) calculating a degree of low luminance dysfunction by calculating a third score representing a difference between the first and second scores.

2. The method recited in claim 1, wherein the second acuity level is lower than the first acuity level and the fourth acuity level is lower than the third acuity level.

3. The method recited in claim 1, further comprising creating conditions for visual dark adaptation in the patient and delaying the continuation of the test for a predetermined amount of time while maintaining the conditions for visual dark adaptation prior to the step of displaying the third character.

4. The method recited in claim 1, wherein the first, second, third, and fourth input signals comprise patient voice responses, and the input device comprises a microphone attached to the computer and voice recognition software implemented on the computer.

5. The method recited in claim 1, wherein at least one of the first, second, third, and fourth characters comprise a non-alphanumeric symbol.

6. The method recited in claim 1, wherein at least one of the first, second, third, and fourth acuity levels are set to a predetermined default value if there are no prior low luminance dysfunction vision test records associated with the patient.

7. The method recited in claim 6, wherein steps (a) through (j) are repeated sequentially using values for the first, second, third, and fourth acuity levels based on the values for the first, second, third, and fourth acuity levels in a prior iteration of the low luminance dysfunction vision test to determine a lowest visual acuity of the patient.

8. The method recited in claim 1, wherein at least one of the first, second, third, and fourth acuity levels are set to a progressive value based on a corresponding acuity level recorded in a prior low luminance dysfunction vision test record associated with the patient.

9. The method recited in claim 8, wherein steps (a) through (j) are repeated sequentially using values for the first, second, third, and fourth acuity levels based on the values for the first, second, third, and fourth acuity levels in a prior iteration of the low luminance dysfunction vision test to determine a lowest visual acuity of the patient.

10. The method recited in claim 1, further comprising comparing the degree of low luminance dysfunction with at least one previously calculated degree of low luminance dysfunction associated with the patient to create a low luminance dysfunction progression report associated with the patient.

11. The method recited in claim 10, wherein the at least one previously calculated degree of low luminance dysfunction associated with the patient was calculated and stored on a computer connected to a computer network.

12. The method recited in claim 1, further comprising storing the degree of low luminance dysfunction in an electronic health record associated with the patient.

13. The method recited in claim 1, further comprising displaying at least one of the degree of low luminance dysfunction, first, second, and third scores with predetermined values for normal low luminance vision, and mild, moderate, and severe degradation associated with dry age-related macular degeneration advancement.

14. The method recited in claim 1, further comprising plotting at least one of the degree of low luminance dysfunction, first score, second score, and third score with corresponding values calculated in at least one previously-administered low luminance dysfunction vision test associated with the patient.

15. The method recited in claim 1, wherein a background color of the display upon which the third and fourth characters are displayed is a color green and the color green and the second luminance level are selected prior to administering the test to replicate night vision goggle-aided vision.

16. The method recited in claim 1, wherein the display comprises a display capable of calibration arranged at a predetermined distance from a chin rest, which chin rest is arranged such that the patient can engage with the chin rest to maintain the predetermined distance from the display and the patient.

\* \* \* \* \*